(12) United States Patent
Min

(10) Patent No.: US 7,972,276 B1
(45) Date of Patent: Jul. 5, 2011

(54) METHOD FOR REMOVING POSTURE DEPENDENCE DURING EVOKED RESPONSE MONITORING OF HF PROGRESSION

(75) Inventor: Xiaoyi Min, Thousand Oaks, CA (US)

(73) Assignee: Pacesetter, Inc., SYlmar, CA (US)

( * ) Notice: Subject to any disclaimer, the term of this patent is extended or adjusted under 35 U.S.C. 154(b) by 409 days.

(21) Appl. No.: 11/740,744

(22) Filed: Apr. 26, 2007

(51) Int. Cl.
*A61B 5/08* (2006.01)
*A61B 5/103* (2006.01)

(52) U.S. Cl. ............. 600/529; 600/547; 607/19; 607/20

(58) Field of Classification Search .................... 607/17, 607/19, 20, 27, 28; 600/509, 529, 547
See application file for complete search history.

(56) References Cited

U.S. PATENT DOCUMENTS

| | | | |
|---|---|---|---|
| 4,712,555 A | 12/1987 | Thornander et al. | |
| 4,788,980 A | 12/1988 | Mann et al. | |
| 4,940,052 A | 7/1990 | Mann et al. | |
| 4,944,298 A | 7/1990 | Sholder | |
| 5,466,254 A | 11/1995 | Helland | |
| 6,308,098 B1 * | 10/2001 | Meyer | 607/17 |
| 6,314,323 B1 | 11/2001 | Ekwall | |
| 6,711,439 B1 | 3/2004 | Bradley et al. | |
| 6,738,666 B1 * | 5/2004 | Park et al. | 607/18 |
| 6,975,904 B1 * | 12/2005 | Sloman | 607/28 |
| 7,336,999 B1 * | 2/2008 | Koh | 607/27 |
| 7,363,085 B1 * | 4/2008 | Benser et al. | 607/42 |

OTHER PUBLICATIONS

Ebner et al., Ventricular evoked response as clinical marker for hemodynamic changes in dilative cardiomyopathy, Pacing Clin Electrophysiol. Feb. 2004;27(2):166-74.

Frey et al., Cardiovascular responses to postural changes: differences with age for women and men, Clin Pharmacol. May 1994;34(5):394-402.

Schuchert et al., Effects of body position and exercise on evoked response signal for automatic threshold activation, Pacing Clin Electrophysiol. Oct. 1999; 22(10):1476-80.

* cited by examiner

Primary Examiner — Carl H Layno
Assistant Examiner — Natasha N Patel

(57) ABSTRACT

An exemplary method includes acquiring intrathoracic impedance values over one or more respiratory cycles, acquiring myocardial evoked response values and assessing cardiac condition based at least in part on the intrathoracic impedance values and the evoked response values. Other exemplary methods, devices, systems, etc., are also disclosed.

17 Claims, 11 Drawing Sheets

EXEMPLARY METHOD 900

PACING SCHEMES
1000

Constant Voltage ($\Delta V = |V_2 - V_1|$)
1010 i decreases as Z increases

Z increases upon standing;
thus, i decreases

Constant Current (i)
1020

$\Delta V$ increases as Z increases

Z increases upon standing;
thus, $\Delta V$ increases

BIPOLAR PACING SCHEMES
1100

METHOD FOR REMOVING POSTURE DEPENDENCE DURING EVOKED RESPONSE MONITORING OF HF PROGRESSION

CROSS-REFERENCE TO RELATED APPLICATIONS

This application is related to and U.S. patent application Ser. No. 10/997,611, filed Nov. 23, 2004, entitled "Data Acquisition for Implantable Cardiac Devices" and U.S. patent application Ser. No. 11/149,058, filed Jun. 6, 2005, entitled "Evoked Response and Impedance Measures for Monitoring Heart Failure and Respiration".

TECHNICAL FIELD

Technologies presented herein generally relate to use of evoked response and impedance measures to monitor patient condition.

BACKGROUND

Many implantable pacing devices have an ability to acquire cardiac electrograms, sometimes referred to as intracardiac electrograms (IEGMs), as a sensing electrode may be positioned in the heart. For example, an implantable pacing device may acquire cardiac electrograms using a case electrode (i.e., case of the device) and a sensing/pacing electrode positioned in the right ventricle. Where the device is implanted in a pectoral pocket, such a "unipolar" sensing configuration may span a distance of over 10 cm. The distance between electrodes in combination with the substantial surface area of the case electrode, make unipolar sensing configurations susceptible to interference from everyday changes in patient physiology. Consequently, useful information contained in the cardiac electrograms may be obscured.

As described herein, various techniques aim to increase usefulness of cardiac electrograms by accounting for patient physiology (e.g., patient position, changes in position, respiration, etc.). Through application of such techniques, information contained in cardiac electrograms may be used for a variety of diagnostics, including hear failure. Further, such diagnostics or information may be used to adjust therapy delivered, for example, by an implantable stimulation device.

SUMMARY

An exemplary method includes acquiring intrathoracic impedance values over one or more respiratory cycles, acquiring myocardial evoked response values and assessing cardiac condition based at least in part on the intrathoracic impedance values and the evoked response values. Other exemplary methods, devices, systems, etc., are also disclosed.

BRIEF DESCRIPTION OF THE DRAWINGS

Features and advantages of the described implementations can be more readily understood by reference to the following description taken in conjunction with the accompanying drawings.

DETAILED DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims.

Overview

Various exemplary methods, devices, systems, etc., disclosed herein aim to increase usefulness of cardiac electrograms. For example, a cardiac electrogram may include information pertaining to an evoked response. An impedance measure may be used to adjust the evoked response to minimize interference from respiration, patient position, etc., to thereby produce an evoked response measure. Further, such a measure may allow for assessment of heart condition (e.g., compared to a threshold or to values over time). Yet further, selection of therapy or adjustment to therapy may rely on such an evoked response measure.

An evoked response measure, as described in more detail below, pertains to any of a variety of characteristics of an evoked response signal as evidenced in a cardiac electrogram (e.g., an IEGM), which may, depending on circumstances, vary with respect to patient position (e.g., supine, prone, etc.). An impedance measure, as described in more detail, pertains to any of a variety of characteristics of an intra-thoracic impedance signal, which may, depending on circumstances and electrode(s) position(s), vary with respect to patient position (e.g., supine, prone, etc) and possibly respiration.

An exemplary stimulation device is described below followed by a discussion of various exemplary mechanisms that rely on one or more evoked response measures to assess cardiac condition (e.g., heart failure, etc.). Various exemplary mechanisms aim to select or adjust therapy in response to such assessment. The aforementioned exemplary stimulation device (described in more detail below) is optionally used to implement various exemplary methods.

Exemplary Stimulation Device

The techniques described below are intended to be implemented in connection with any stimulation device that is configured or configurable to stimulate nerves, stimulate muscle tissue and/or stimulate and/or shock a patient's heart (e.g., myocardial muscle tissue).

Figure 1:
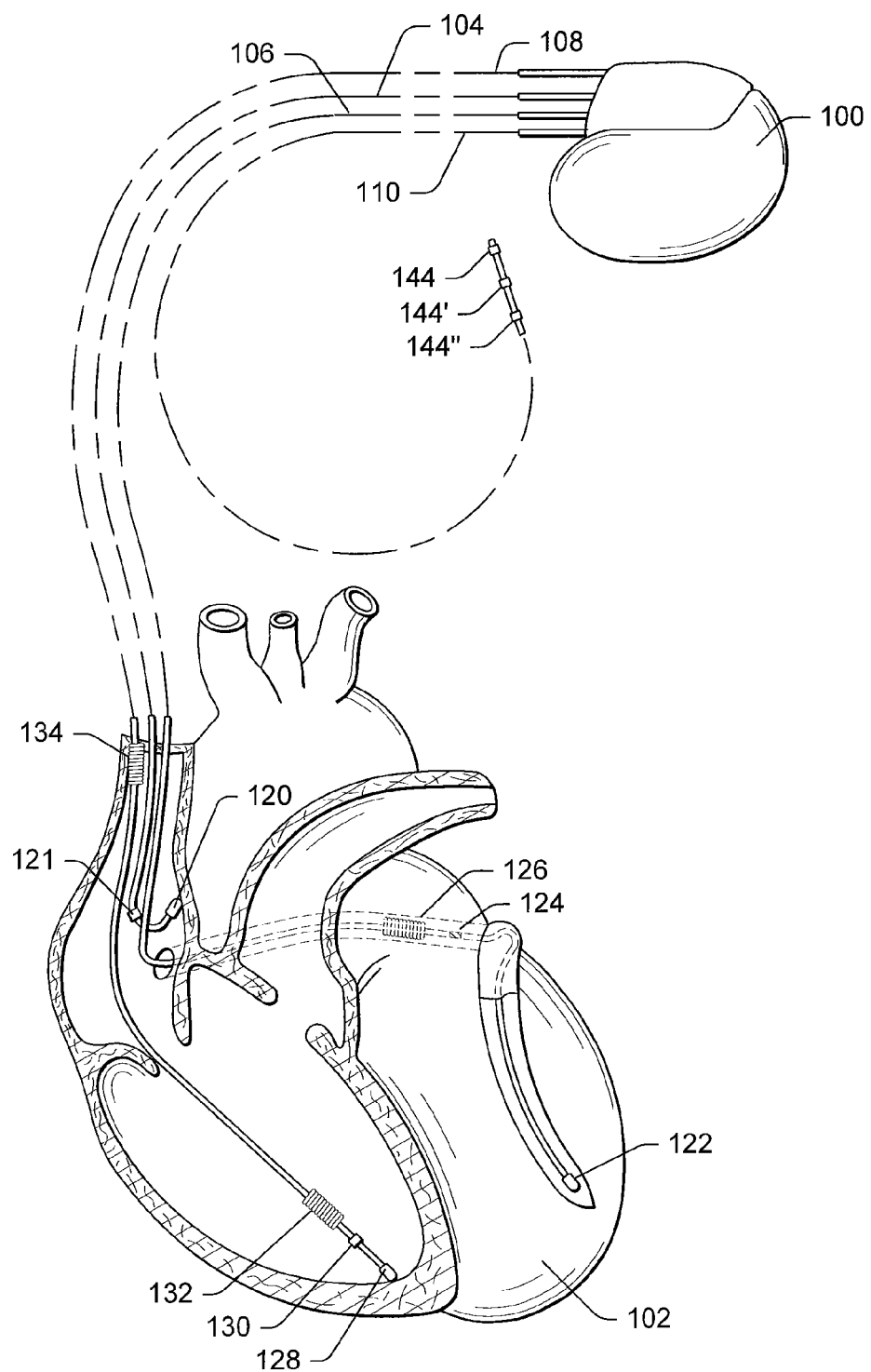
FIG. 1 is a simplified diagram illustrating an exemplary implantable stimulation device in electrical communication with at least three leads implanted into a patient's heart and at least one other lead for delivering stimulation and/or shock therapy. Exemplary devices may have lesser leads as well.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of nerves (e.g., autonomic nerves, phrenic nerves, etc.) and/or muscle tissue other than myocardial tissue. In addition, the device 100 includes a fourth lead 110 having, in this implementation, three electrodes 144, 144', 144" suitable for stimulation of nerves (e.g., autonomic nerves, phrenic nerves, etc.) and/or muscle and/or detection of other physiologic signals that may be used by the implanted system to modify stimulation parameters or diagnose patient condition. The lead 110 may be positioned in and/or near a patient's heart, near a nerve (e.g., an autonomic nerve, a phrenic nerve, etc.) or near muscle tissue other than myocardial tissue within a patient's body and remote from the heart. The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of nerves and/or muscle tissue.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of autonomic nerves, other nerves and/or tissue. Such a lead may include cardiac pacing, nerve and/or muscle stimulation functionality and may further include bifurcations or legs. For example, an exemplary coronary sinus lead includes pacing electrodes capable of delivering pacing pulses to a patient's left ventricle and at least one electrode capable of stimulating a nerve (e.g., autonomic nerve, a phrenic nerve, etc.) and/or other tissue.

The stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating a nerve and/or other tissue; such an electrode may be positioned on the lead or a bifurcation or leg of the lead. For example, an exemplary right ventricular lead includes pacing electrodes capable of delivering pacing pulses to a patient's left ventricle and at least one electrode capable of stimulating a nerve (e.g., autonomic nerve, a phrenic nerve, etc.) and/or other tissue.

Figure 2:
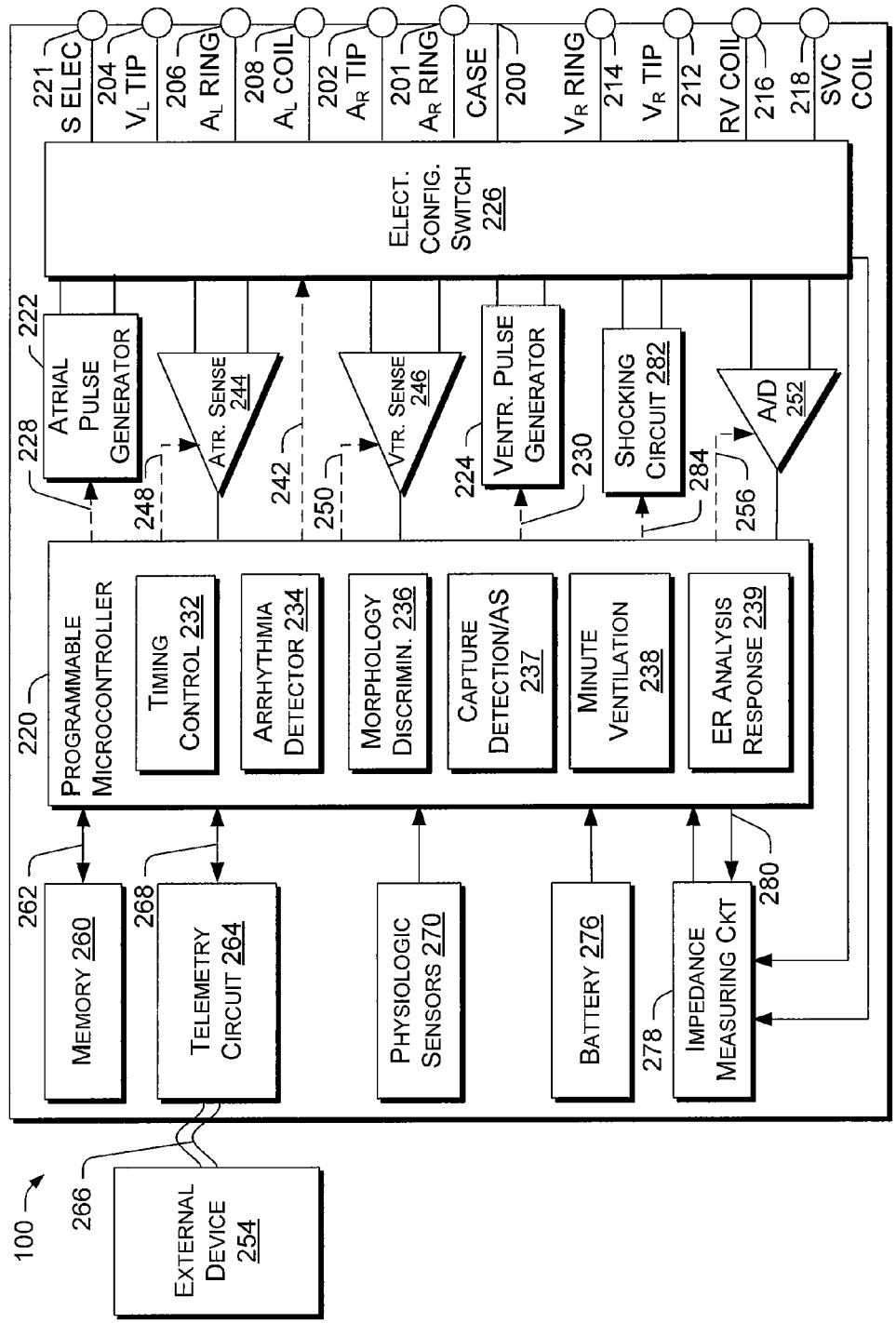
FIG. 2 is a functional block diagram of an exemplary implantable stimulation device illustrating basic elements that are configured to provide cardioversion, defibrillation, pacing stimulation and/or autonomic nerve stimulation or other tissue and/or nerve stimulation. The implantable stimulation device is further configured to measure position and/or movement.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to nerves (e.g., autonomic nerves, phrenic nerves, etc.) and/or muscle tissues. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, and/or autonomic nerve stimulation and/or treating respiratory issues via cardiac, nerve and/or muscle stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or autonomic stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing, shocking, and/or autonomic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable nerve and/or muscle stimulation electrodes is also possible via these and/or other terminals (e.g., via a stimulation terminal S ELEC 221).

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable nerve and/or muscle stimulation electrodes is also possible via these and/or other terminals (e.g., via the stimulation terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to nerves and/or other muscle tissue) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, interatrial conduction (A-A) delay, or interventricular conduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes, for example, an arrhythmia detector 234, a morphology discrimination module 236, a capture detection and/or autosensitivity module 237, a minute ventilation (MV) response module 238 and an evoked response analysis module 239. These components can be utilized by the stimulation device 100 for determining desirable times to administer various therapies. The aforementioned components may be implemented in hardware as part of the microcontroller 220, or as software/firmware instructions programmed into the device and executed on the microcontroller 220 during certain modes of operation. Various exemplary methods described herein are optionally implemented as logic, which may be embodied in software and/or hardware.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture. The sensing circuits 244, 246, via switches, etc., may also be used to sense information related to respiration (e.g., chest movement monitoring, etc.).

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture (e.g., an evoked response) has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. Other features for arrhythmia detection, confirmation, etc. are discussed below and may be suitable as appropriate. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation) are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy"). Similar rules can be applied to the atrial channel to determine if there is an atrial tachyarrhythmia or atrial fibrillation with appropriate classification and intervention.

Nerve, muscle and/or cardiac signals are also optionally applied to inputs of an analog-to-digital (A/D) data acquisition system 252. The data acquisition system 252 is, for example, configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve and/or muscle stimulation lead through the switch 226 to sample signals across any of desired electrode (e.g., unipolar) or electrodes (e.g., multipolar).

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further includes one or more physiologic sensors 270. For example, a physiologic sensor commonly referred to as a "rate-responsive" sensor is optionally included and used to adjust pacing stimulation rate according to the exercise state of the patient. However, one or more of the physiologic sensors 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, diurnal changes in activity (e.g., detecting sleep and wake states), etc. Accordingly, the microcontroller 220 responds by adjusting the various pacing parameters (such as rate, AV Delay, V-V Delay, etc.) at which the atrial and ventricular pulse generators, 222 and 224, generate stimulation pulses.

While shown as being included within the stimulation device 100, it is to be understood that the one or more physiologic sensors 270 may also be external to the stimulation device 100, yet still be implanted within or carried by the patient.

In particular, the one or more physiologic sensors 270 optionally include a position and/or movement sensor mounted within the housing 200 of the stimulation device 100 to detect movement in the patient's position or the patient's position. Such a sensor may operate in conjunction with a position and/or movement analysis module (e.g., executable in conjunction with the microcontroller 220). The position and/or movement sensor may be implemented in many ways. In one particular implementation, the position sensor is implemented as an accelerometer-based sensor capable of measuring acceleration, position, etc. For example, such a sensor may be capable of measuring dynamic acceleration and/or static acceleration. In general, movement of the patient will result in a signal from the accelerometer. For example, such an accelerometer-based sensor can provide a signal to the microcontroller 220 that can be processed to indicate that the patient is undergoing heightened physical exertion, moving directionally upwards or downwards, etc.

Accelerometers typically include two or three sensors aligned along orthogonal axes. For example, a commercially available micro-electromechanical system (MEMS) marketed as the ADXL202 by Analog Devices, Inc. (Norwood, Mass.) has a mass of about 5 grams and a 14 lead CERPAK (approx. 10 mm by 10 mm by 5 mm or a volume of approx. 500 mm3). The ADXL202 MEMS is a dual-axis accelerometer on a single monolithic integrated circuit and includes polysilicon springs that provide a resistance against acceleration forces. Such a sensor may measure tilt, for example, the ADXL202 is most sensitive to tilt when its sensitive axes are perpendicular to the force of gravity, i.e., parallel to the earth's surface. The term MEMS has been defined generally as a system or device having micro-circuitry on a tiny silicon chip into which some mechanical device such as a mirror or a sensor has been manufactured. The aforementioned ADXL202 MEMS includes micro-circuitry and a mechanical oscillator.

Further, depending on position of the implanted device and such a movement sensor, the sensor may measure or monitor chest movement indicative of respiratory characteristics. For example, for a typical implant in the upper chest, upon inspiration, the upper chest expands thereby causing the implanted device to move. Accordingly, upon expiration, the contraction of the upper chest causes the device to move again. Such a movement sensor may sense information capable of distinguishing whether a patient is horizontal, vertical, etc.

While respiratory information may be obtained via the one or more physiologic sensors 270, the aforementioned minute ventilation (MV) sensor 238 may sense respiratory information related to minute ventilation, which is defined as the total volume of air that moves in and out of a patient's lungs in a minute. A typical MV sensor uses thoracic impedance, which is a measure of impedance across the chest cavity wherein lungs filled with air have higher impedance than empty lungs.

Thus, upon inhalation, impedance increases; whereas upon exhalation, impedance decreases.

With respect to impedance measurement electrode configurations, a right ventricular tip electrode and case electrode may provide current while a right ventricular ring electrode and case electrode may allow for potential sensing. Of course, other configurations and/or arrangements may be used to acquire measurements over other paths (e.g., a superior-inferior path and a left-right path, etc.). Multiple measurements may be used wherein each measurement has a corresponding path. Further, measurement configurations for impedance may be bipolar, tripolar or other multipolar.

Direct measurement of phrenic nerve activity may be achieved using a cuff or other suitable electrode appropriately positioned in relationship to a phrenic nerve. For example, a cuff electrode substantially surrounding the right phrenic nerve in the thoracic cavity can detect signals indicative of intrinsic respiratory drive (at least to the right hemidiaphragm). Such signals are typically of amplitude measured in microvolts (e.g., less than approximately 30 microvolts). Sensing may be coordinated with other events, whether natural event or events related to some form of stimulation therapy. As discussed herein, some degree of synchronization may occur between calling for and/or delivering stimulation for diaphragm activation and sensing of neural activity and/or other indicators of respiration and, in particular, inspiration.

While respiratory characteristics are optionally measured with a signal such as a thoracic impedance signal, alternatively or in addition to, central respiratory drive is optionally determined via sensing of phrenic nerve activity. In one example, phrenic nerve (e.g., right and/or left phrenic nerve) activity is sensed using one or more electrodes on or proximate to the phrenic nerve. In another example, diaphragmatic myopotentials are sensed (e.g., EMG, etc.) using one or more electrodes on or proximate to the diaphragm. Plethysmography may be used in measuring any of a variety of variables that are related to respiration.

Other means for detection include measuring the intrathoracic pressure associated with respiration or from stress and/or strain gauges measuring changes in the dimensions of the thoracic cavity including the lungs. Respiratory information may also be inferred by sensing information that relates to mechanisms altered by respiration. For example, body chemistry varies in response to respiration. Hence, chemical parameters such as tissue or blood pH, $PCO_2$, $O_2$, $PO_2$ may be sensed and either used to infer, confirm and/or augment other respiratory information.

Signals generated by the one or more physiologic sensors 270 and/or the MV sensor 238 or impedance sensor are optionally processed by the microcontroller 220 in determining whether to apply one or more therapies.

More specifically, with respect to a movement sensor, the microcontroller 220 may receive a signal from an accelerometer-based sensor that may be processed to produce an acceleration component along a vertical axis (i.e., z-axis signal). This acceleration component may be used to determine whether there is an increased or decreased level of activity in the patient, etc. The microcontroller 220 optionally integrates such a signal over time to produce a velocity component along the vertical direction. The vertical velocity may be used to determine a patient's position/activity aspects as well, such as whether the patient is going upstairs or downstairs. If the patient is going upstairs, the microcontroller 220 may increase the pacing rate or invoke an orthostatic compensator to apply a prescribed stimulation therapy, especially at the onset. If the patient is traversing downstairs, the device might decrease a pacing rate or perhaps invoke the MV response module to control one or more therapies during the descent. The MV response module may provide information to be used in determining a suitable pacing rate by, for example, measuring the thoracic impedance from the MV sensor 238, computing the current MV, and comparing that with a long-term average of MV. As described herein, MV information and/or other sensed information may be used to determine an appropriate respiratory therapy.

The microcontroller 220 can also monitor one or more of the sensor signals for any indication that the patient has moved from a supine position to a prone or upright position. For example, the integrated velocity signal computed from the vertical acceleration component of the sensor data may be used to determine that the patient has just stood up from a chair or sat up in bed. A sudden change in the vertical signal (e.g., a positive change in a direction normal to the surface of the earth), particularly following a prolonged period with little activity while the patient is sleeping or resting, confirms that a posture-changing event occurred. The microcontroller 220 optionally uses this information as one potential condition for deciding whether to invoke, for example, an orthostatic compensator to apply cardiac pacing therapy for treating orthostatic hypotension. Other uses are described in more detail below.

While a two-axis accelerometer may adequately detect tilt with respect to acceleration of gravity, the exemplary stimulation device 100 may also or alternatively be equipped with a GMR (giant magnetoresistance) sensor and circuitry that detects the earth's magnetic fields. Such a GMR sensor and circuitry may be used to ascertain absolute orientation coordinates based on the earth's magnetic fields. The device is thus able to discern a true vertical direction regardless of the patient's position (i.e., whether the patient is lying down or standing up). Where three-axes are measured by various sensors, coordinates may then be taken relative to the absolute orientation coordinates from the GMR. For instance, as a person sits up, the axial coordinates of an accelerometer-based sensor might change by 90°, but the sensor signals may be calibrated as to the true vertical direction based on the output of a GMR sensor and circuitry. Other sensors for position may include three sensors that are placed orthogonally to one another to detect the gravitational force and hence device position.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration rate and/or tidal volume; measuring thoracic or other impedances for determining shock or other thresholds; detecting when the device has been implanted; measuring stroke volume; and detecting the opening of heart valves, etc. The impedance measuring circuit 278 is advantageously coupled to the switch 226 so that any desired electrode may be used.

The impedance measuring circuit 278 may also measure impedance related to lung inflation. Such a circuit may use a case electrode, an electrode positioned in or proximate to the heart and/or another electrode positioned within or proximate to the chest cavity. Various exemplary methods described below rely on impedance measurements to determine lung inflation and/or optionally inspiratory vagal excitation, which can inhibit excitatory signals to various muscles (e.g., diaphragm, external intercostals, etc.).

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

The evoked response analysis module 239 may make determinations as to changes in heart condition (e.g., heart failure) or provide other functionality to aid in the implementation of various exemplary methods described herein. The evoked response analysis module 239 may call for and/or receive information from other modules or circuits. For example, the module 239 may receive information from the impedance measuring circuit 278, one or more physiologic sensors 270, the capture detection module 237, etc.

Figure 3:
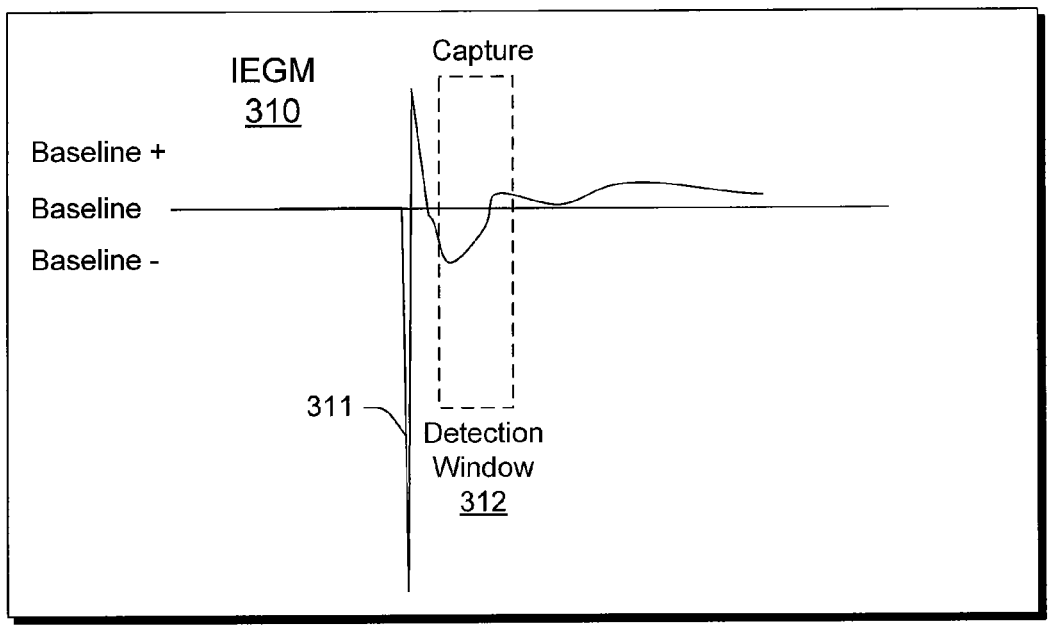
FIG. 3 is a series of plots corresponding to various evoked response scenarios.
Figure 3:
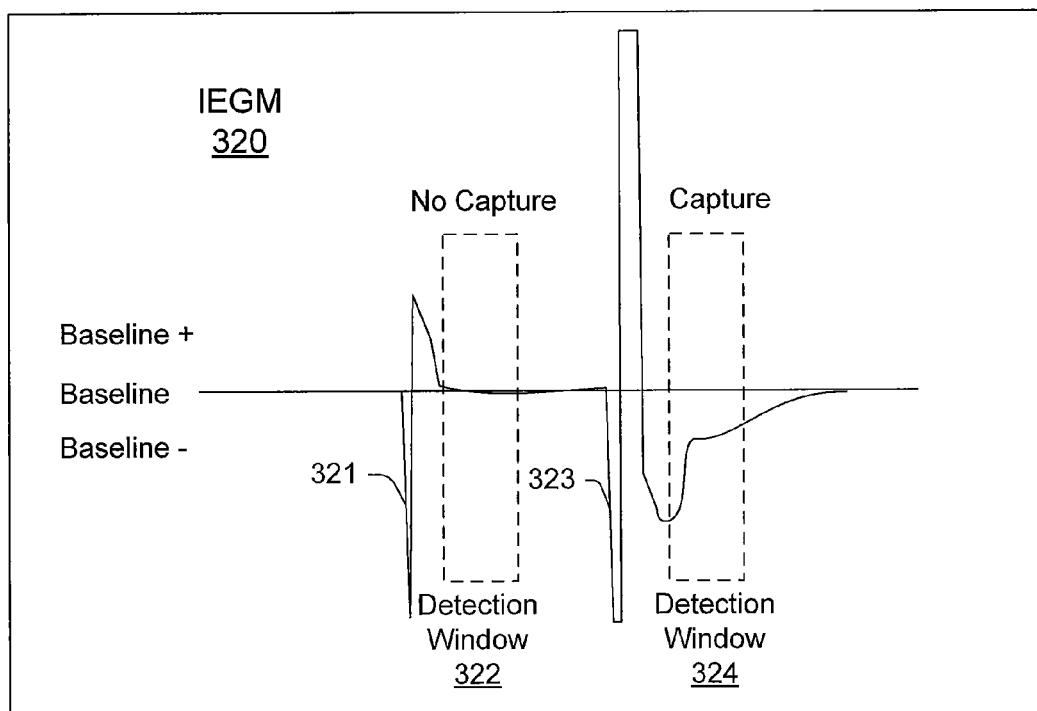

FIG. 3 shows various evoked response scenarios 300. As described above, an implantable device can acquire information as to electrical activity of the heart. Such information may be acquired using any of a variety of electrode configurations (e.g., unipolar, bipolar, multipolar) and, regardless of the configuration, is typically referred to as an intracardiac electrogram (IEGM). If pacing or other stimulation is delivered to the heart, then various techniques can be used to avoid sensing the delivered stimulation energy (e.g., blanking, etc.). In some instances, an implantable device implements an evoked response detection window that commences after delivery of a stimulus and terminates prior to delivery of a subsequent stimulus. For example, an automatic capture detection algorithm referred to as AUTOCAPTURE™ aims to detect an evoked response within a detection window that spans from about 15 ms to about 65 ms after delivery of a pacing stimulus. Such an algorithm may be implemented via the aforementioned capture detection module 237 or the evoked response analysis module 239 or both modules.

Referring to the IEGM plot 310, delivery of stimulation energy occurs that causes a large deviation in the sensed potential from a baseline value, which may be referred to as a pacing spike 311. In the example of the plot 310, the spike 311 deviates negatively from the baseline; however, this depends on the polarization of the stimulus as well as the configuration of the sensing circuit (e.g., electrode configuration, etc.). At some point after the spike 311, the implantable device implements a detection window 312.

A device may acquire an entire IEGM, a partial IEGM and/or select a portion of an acquired IEGM for purposes of evoked response detection. Various techniques exist for deciding whether an evoked response occurred in response to a stimulus. For example, a technique may use morphology of IEGM information, slope of IEGM information, amplitude(s) of IEGM information and/or integral of IEGM information with respect to time to decide whether an evoked response occurred. In the example of the plot 310, the IEGM information present within the detection window 312 is typically sufficient to conclude that an evoked response occurred that caused depolarization of the heart (i.e., capture).

The IEGM plot 320 shows another scenario where an initial stimulus (e.g., spike 321) does not cause an evoked response or capture (see, e.g., detection window 322) and where a subsequent, back-up stimulus (e.g., spike 323), delivered at higher stimulation energy than the initial stimulus, causes an evoked response (see, e.g., detection window 324). In general, a back-up stimulus uses a stimulation energy that aims to guarantee an evoked response. The spike 323 is clipped due to configuration of the IEGM sensing circuit (e.g., circuit 246 or circuit 252). Configuration parameters for an IEGM sensing circuit may include gain, off-set, etc.

A comparison between the IEGM information of the detection window 312 and the detection window 324 demonstrates that an evoked response depends on the nature of the stimulus energy. While, the examples of FIG. 3 pertain to pacing stimuli delivered using a "constant voltage" technique; pacing voltage is not necessarily constant, as for pacing stimuli, voltage may vary due to capture threshold. Further, a back-up stimulus typically uses a near maximal pacing stimulus voltage. Another technique, referred to as "constant current", is discussed further below along with differences between constant voltage and constant current techniques.

In addition to voltage, various other factors can affect an evoked response as well. For example, patient condition, patient drug use (e.g., ajmaline—a plant alkaloid that can change the shape and threshold of cardiac action potentials) and patient position can affect evoked responses. As described herein, an evoked response measure is used to assess cardiac condition such as heart failure. Further, various exemplary techniques are described herein that allow for reducing the effect of patient position on such evoked response based assessments.

Figure 4:
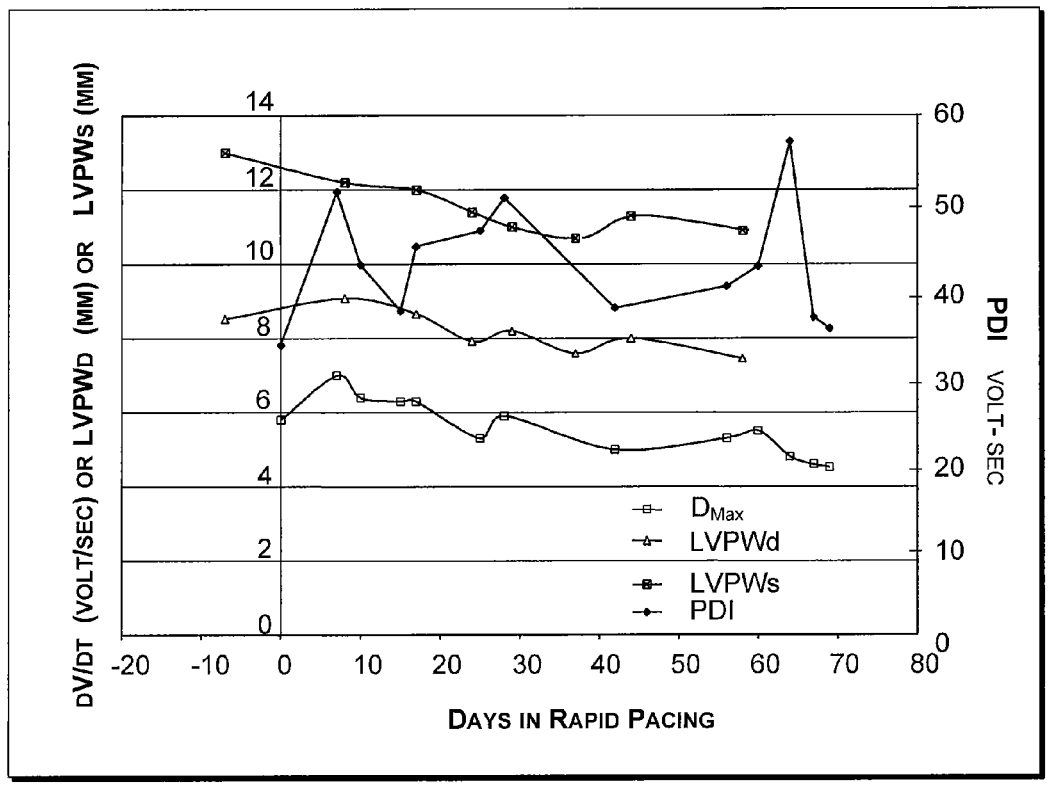
FIG. 4 is an exemplary plot of various evoked response measures versus time as related to progression of heart failure.

FIG. 4 shows an exemplary plot 400 of evoked response information including depolarization integral and maximum derivative of depolarization signal with respect to time during progression of heart failure in comparison to the posterior wall thickness of the left ventricle. More specifically, the plot 400 includes conduction velocity data from a mammalian model for depolarization integral (PDI) in volts-s, maximum time derivative of the depolarization signal ($D_{Max}$) in volts per second, left ventricular posterior wall in diastolic (LVPWd) in millimeters and left ventricular posterior wall in systolic (LVPWs) in millimeters versus days in rapid pacing. These data indicate that $D_{Max}$, LVPWd and LVPWs values decrease as heart failure progresses; however, the data for PDI may not allow for a firm conclusion because the data exhibits noise due to problems such as those discussed with reference to the evoked response scenarios 300 of FIG. 3 (e.g., patient position). In addition, noise exists in the $D_{Max}$ data for same or similar reasons, further a fairly substantial correlation exists between decrease in wall thickness and decrease in $D_{Max}$. In general, the plot 400 supports the existence of a substantial correlation between progression of heart failure and PDI and/or $D_{Max}$. Consequently, various exemplary mechanisms described herein may allow for a more robust measure of the progression of heart failure.

A study by Ebner et al. ("Ventricular evoked response as clinical marker for hemodynamic changes in dilative cardiomyopathy", Pacing Clin Electrophysiol. 2004 February; 27(2):166-74), reported a significant correlation between an evoked response measure and NYHA class. More specifically, the study of Ebner et al., reported that two evoked response measures (R(ER) and T(ER)) were significantly reduced in NYHA Class IV patients (P<0.05), and nearly significantly reduced in DCM versus other patients (P=0.05-0.09) and concluded that analysis of evoked response parameters bears a promising potential for dynamic monitoring of diseases affecting the hemodynamics, and of therapeutic effects, by means of regular, nonburdening pacemaker follow-up examinations.

The data of the plot 400 and the study of Ebner et al., demonstrate that evoked response measures can provide valuable information for use in assessing patient condition. However, patient position can introduce significant "noise", which unaccounted for, can greatly reduce or obfuscate information indicative of patient condition (e.g., cardiac condition).

Figure 5:
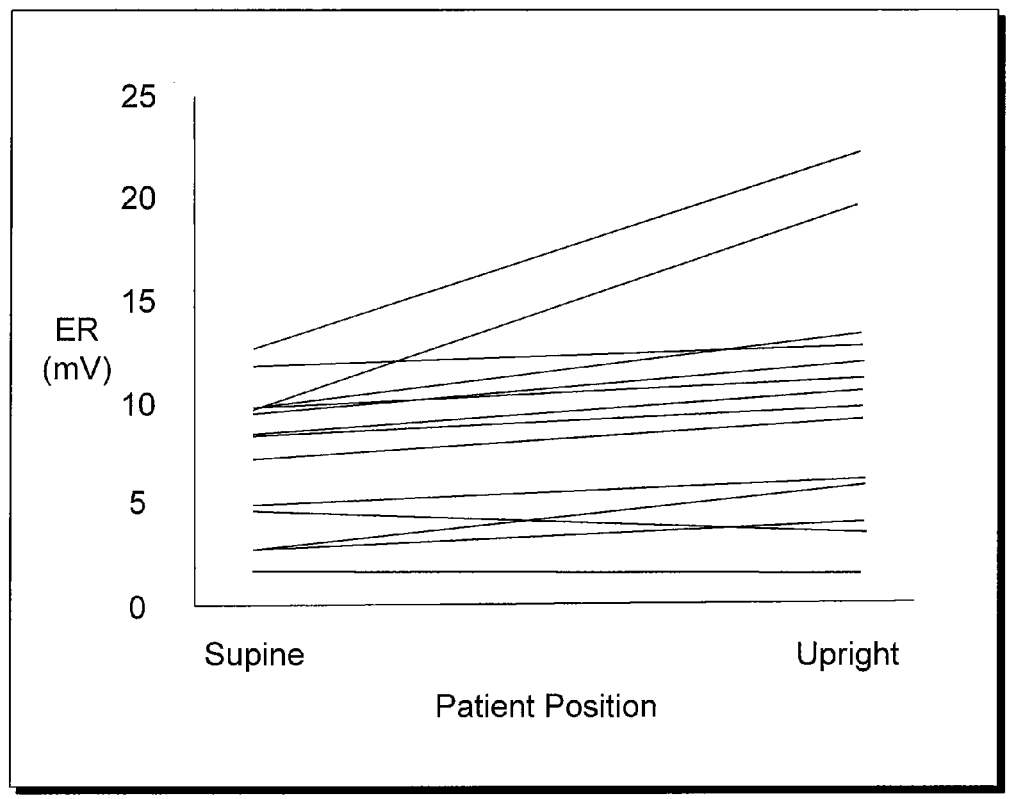
FIG. 5 is a plot of evoked response amplitude versus patient position for various patients.

FIG. 5 shows a plot 500 of evoked response amplitude (mV) versus patient position. These data were presented in a study by Schuchert et al., "Effects of body position and exercise on evoked response signal for automatic threshold activation", *Pacing Clin Electrophysiol.* 1999 October; 22(10):1476-80. The study included 14 patients with a VVIR mode REGENCY® SR+pacemaker (St. Jude Medical Inc., Sylmar, California) who had received one of the following ventricular pacing leads Membrane E 1450 T (n=8) (St. Jude Medical Inc.), CapSure Z 5034 (n=4) (Medtronic Inc., Minneapolis, Minn.) or SX 60 (n=2) (Biotronik GmbH & Co. KG, Berlin, Germany). The evoked response signal was 7.4+/−3.3 mV during supine and increased to 9.7+/−5.6 mV during upright position (P<0.05); about a 35% increase in the evoked response amplitude. More specifically, as discussed herein, evoked response amplitude is related to position of the heart in relation to the bipolar detection field of the pacing lead. Thus, as shown in the plot 500, the amplitude of the evoked response is typically greater for a patient in an upright position than for the patient in a supine position.

While various implantable devices can acquire evoked responses (e.g., via IEGM information) caused by delivery of a stimulus to a single pacing site, an implantable device capable of multichamber pacing may acquire evoked responses from one or more sites. For example, an implantable device capable of delivering stimuli to the left ventricle and to the right ventricle may be capable of acquiring a left ventricular evoked response and a right ventricular evoked response. Further, a single sensing channel may be used or, depending on device capabilities, multiple sensing channels may be used (e.g., a right ventricular sensing channel and a left ventricular sensing channel).

Recently, automatic capture algorithms have been developed for implantable bi-ventricular pacing devices that can deliver cardiac resynchronization therapy. Where therapy involves bi-ventricular pacing, such devices can routinely acquire right ventricular evoked responses and left ventricular evoked responses. Hence, additional information may be available for assessing cardiac condition. Further, such information may be used to determine one or more multichamber pacing parameter (e.g., $AV_{RV}$ delay, $AV_{LV}$ delay, VV delay, etc.). As described herein, various exemplary techniques can be used with single chamber pacing therapies as well as multichamber pacing therapies.

Figure 6:
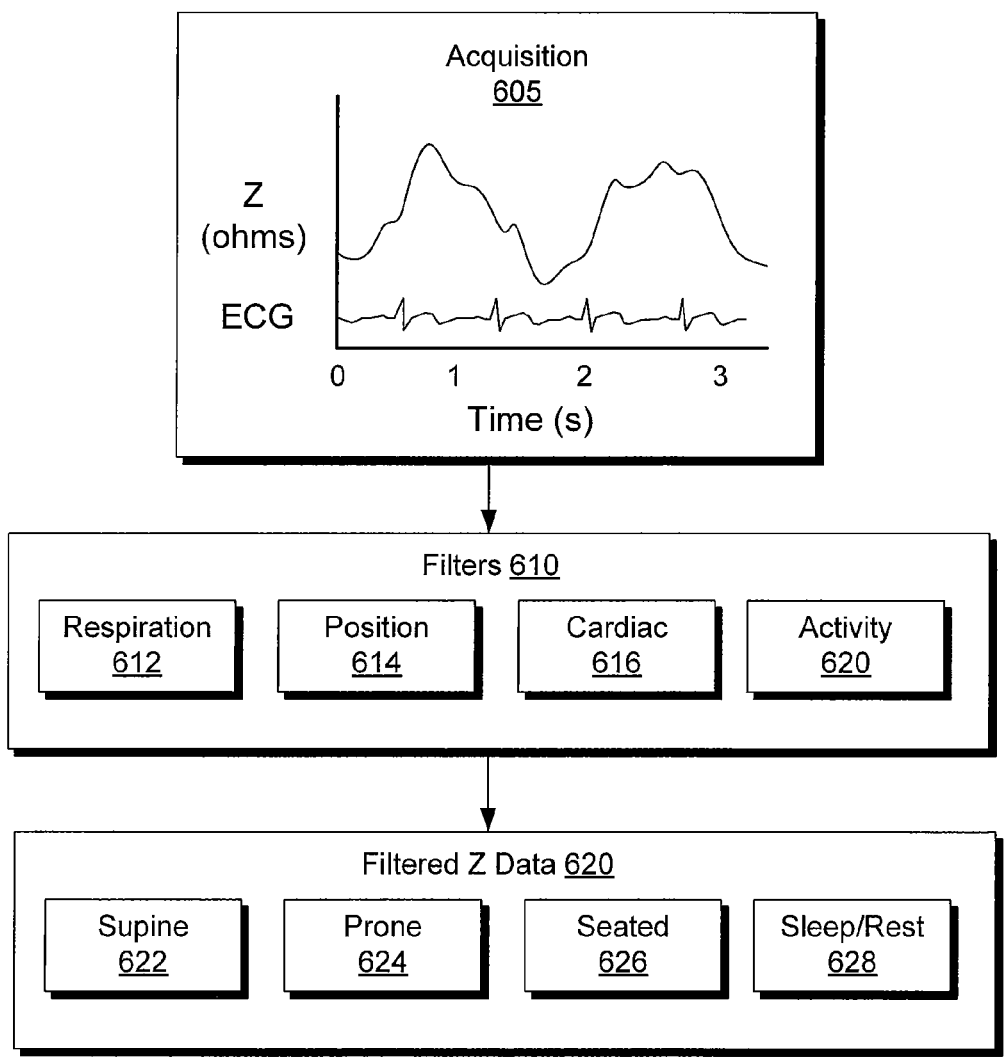
FIG. 6 is a block diagram of an exemplary method for analyzing impedance information.

As already mentioned, impedance measurements may be used to provide information as to a variety of conditions, including patient posture. FIG. 6 shows an exemplary method 600 for using impedance information. An acquisition step 605 acquires data, as indicated by a plot of impedance values versus time over a period of a couple of respiratory cycles. In this example, two respiratory cycles occur over about 3 to 4 seconds where respiration causes changes to impedance. In addition, over the same period of time, the heart beats around 4 to 5 times, which also affects impedance. Further, patient position and patient activity can affect impedance as well. To more effectively use information contained in impedance versus time data, the method 600 includes use of one or more filters 610 to filter the impedance data.

The filters 610 include a respiration filter 612, a position filter 614, a cardiac filter 616, and a patient activity filter 620. These filters may be applied to the data for the purpose of determining patient state or condition. For example, a respiration filter may rely on subtracting a sinusoid shape from impedance versus time data. The resulting filtered data (e.g., the filtered data 620) may then be used to distinguish patient position (e.g., supine 622, prone 624, seated 626, etc.) and/or patient activity (e.g., sleep/rest 628).

An exemplary method includes positioning a patient, acquiring impedance versus time data, filtering the data using one or more filters and then analyzing the filtered data to determine whether impedance versus time data may be used to detect patient position. In a particular example, a patient is positioned in various postures: supine, supine 45°, left side supine, right side supine and prone. For each of the positions, impedance signals are acquired using, for example, a case and right atrial ring electrode configuration for current and a case and right atrial tip electrode for potential measurement. An analysis follows that may include filtering to determine whether impedance data can be used for one or more purposes such as determining patient position, activity, condition, etc. As described herein, impedance data may be used in conjunction with evoked response data to determine or more accurately determine patient condition. While impedance is mentioned, in practice values may be potential, resistance or in another form related to impedance.

As already mentioned, and shown in FIG. 6, impedance measurements include a cardiac component and a respiratory component, which may both be affected to some extent by patient posture. In general, the cardiac component varies according to the cardiac cycle and the respiratory component varies according to the respiratory cycle, which is typically less frequent. An impedance measurement may be segregated into a cardiac component and a respiratory component using cycle information. Further, a ratio of respiratory component to cardiac component may be useful in assessing a patient's condition.

The relationship between posture and thoracic impedance has been reported in various studies. For example, Frey et al. ("Cardiovascular responses to postural changes: differences with age for women and men", Clin Pharmacol. 1994 May; 34(5):394-402) made measurements after 10 minutes in each of supine, seated, and standing positions in 22 men and 25 women who ranged in age from 21 to 59 years. The study of Frey et al. noted that, on rising, subjects' diastolic and mean arterial pressures, heart rate, total peripheral resistance (TPR), and thoracic impedance increased; cardiac output, stroke volume, and mean stroke ejection rate decreased; and changes in all variables, except heart rate, were greater from supine to sitting than sitting to standing.

Thus, while various examples discussed herein pertain to using intrathoracic impedance information in conjunction with evoked response information to assess cardiac condition, intrathoracic impedance, as it relates to patient position, may be used for various other purposes as well.

As described herein, various exemplary techniques use impedance information (e.g., acquired impedance data) to adjust evoked response information (e.g., acquired evoked response data). For example, such a technique can allow for more accurate comparisons of evoked response data acquired at different patient positions.

An exemplary method includes acquiring intrathoracic impedance values over one or more respiratory cycles, acquiring myocardial evoked response values and assessing cardiac condition based at least in part on the intrathoracic impedance values and the evoked response values. For example, the intrathoracic impedance values can be used to adjust the myocardial evoked response values to reduce patient position effects. As patient position effects are reduced, underlying effects of cardiac condition become more apparent. Such a method may include acquiring intrathoracic impedance values using an electrode configuration that includes a case or can electrode (e.g., unipolar configuration). An electrode configuration used to acquire impedance information may be used to acquire evoked response information, i.e., the impedance vector and the evoked response sensing vector may be the same vector. In such a manner, the effect of impedance may be removed from an evoked response measurement, which can be beneficial when patient position is unknown.

A method may apply one or more statistical techniques to impedance data. For example, an exemplary method includes adjusting one or more of evoked response values using an average intrathoracic impedance value where the average intrathoracic impedance value is an average of intrathoracic impedance values acquired over one or more respiratory cycles. An average of intrathoracic impedance values acquired over one or more respiratory cycles may be calculated to reduce variations in impedance due to respiration.

A method may apply one or more statistical techniques to evoked response data. For example, evoked response data may be averaged over a respiratory cycle to reduce effects of respiration on the evoked response data. An exemplary method may average intrathoracic impedance values over a respiratory cycle and evoked response values over a respiratory cycle. In another example, acquisition of intrathoracic impedance values and evoked response values may occur on a beat-to-beat basis. In such an example, intrathoracic impedance values and evoked response values can be averaged for a given time period (e.g., during which a patient is in a particular position).

A method may determine a nominal intrathoracic impedance value. For example, a nominal impedance value may be determined using impedance values acquired while a patient is in a known position and activity state (e.g., supine and sleeping or resting, etc.). In another example, a method uses one or more intrathoracic impedance values to deciding if a patient is in a supine position or a prone position (e.g., standing or seated). For example, a nominal intrathoracic impedance value and an average of intrathoracic impedance values acquired over one or more respiratory cycles may be compared to decide if a patient has changed position (e.g., prone to supine, supine to prone, etc.).

As described in more detail below, an exemplary method may include adjusting one or more of evoked response values based at least in part on a difference between a nominal intrathoracic impedance value and an average of intrathoracic impedance values. For example, a percentage change from a nominal impedance value may be used to adjust one or more evoked response value. In general, when a patient moves from a supine position to a prone position, evoked response amplitude increases as does intrathoracic impedance; thus, a change in intrathoracic impedance may be used to adjust a prone evoked response value or measure such that the measure may be compared or analyzed with other evoked response values acquired while the patient is in a supine position.

An exemplary method can include acquiring intrathoracic impedance values over one or more respiratory cycles for a patient in at least a first position and a second position. For example, a method includes acquiring intrathoracic impedance values over one or more respiratory cycles for a patient in a prone position and acquiring intrathoracic impedance values over one or more respiratory cycles for a patient in a supine position. Such a method may determine a difference between the intrathroacic impedance values for the patient in the prone position and for the patient in the supine position and then adjust one or more evoked response values using the difference.

Figure 10:
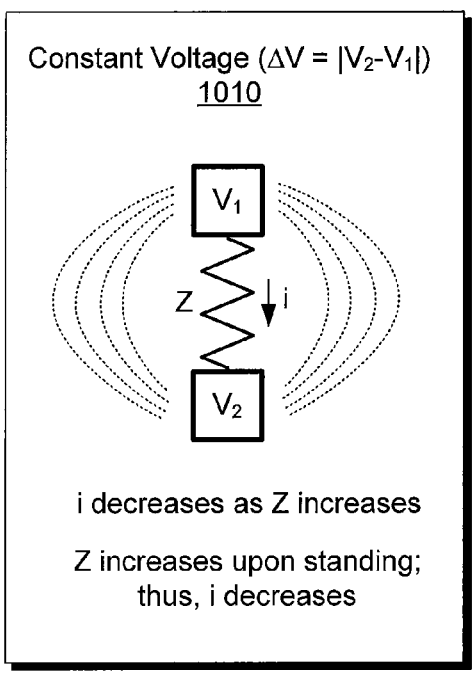
FIG. 10 is a diagram of a constant voltage pacing scheme and a constant current pacing scheme.
Figure 10:
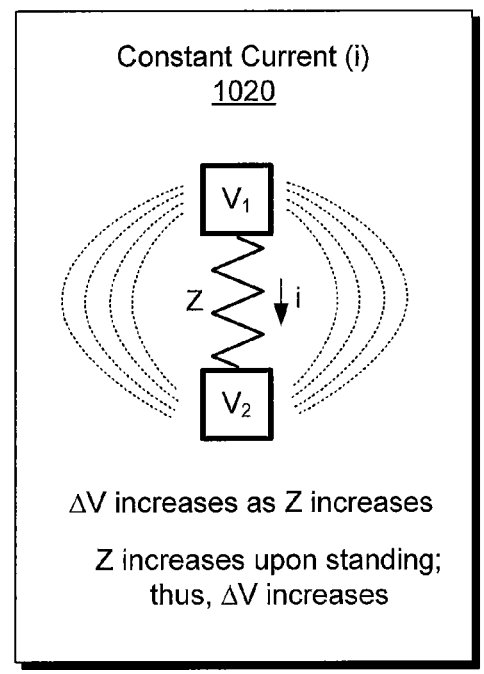

With respect to evoked responses, acquisition may occur following a stimulus delivered using constant current scheme or a stimulus delivered using a constant voltage scheme (see, e.g., FIG. 10). A stimulus may be delivered using a bipolar electrode configuration or other electrode configuration. Where an implantable device delivers cardiac pacing therapy, an assessment of cardiac condition that relies on evoked response (e.g., an impedance adjusted evoked response), control logic of the device may decide whether to adjust a cardiac pacing therapy based on the assessment. As already mentioned with respect to FIG. 2, control logic is optionally implemented through use of a microprocessor and instructions stored on one or more computer-readable media.

An exemplary implantable device includes a processor, memory and control logic to call for acquiring intrathoracic impedance values over one or more respiratory cycles, to call for acquiring myocardial evoked response values and to assess cardiac condition based at least in part on acquired intrathoracic impedance values and acquired evoked response values. The control logic optionally relies on processor executable instructions stored in the memory.

Figure 7:
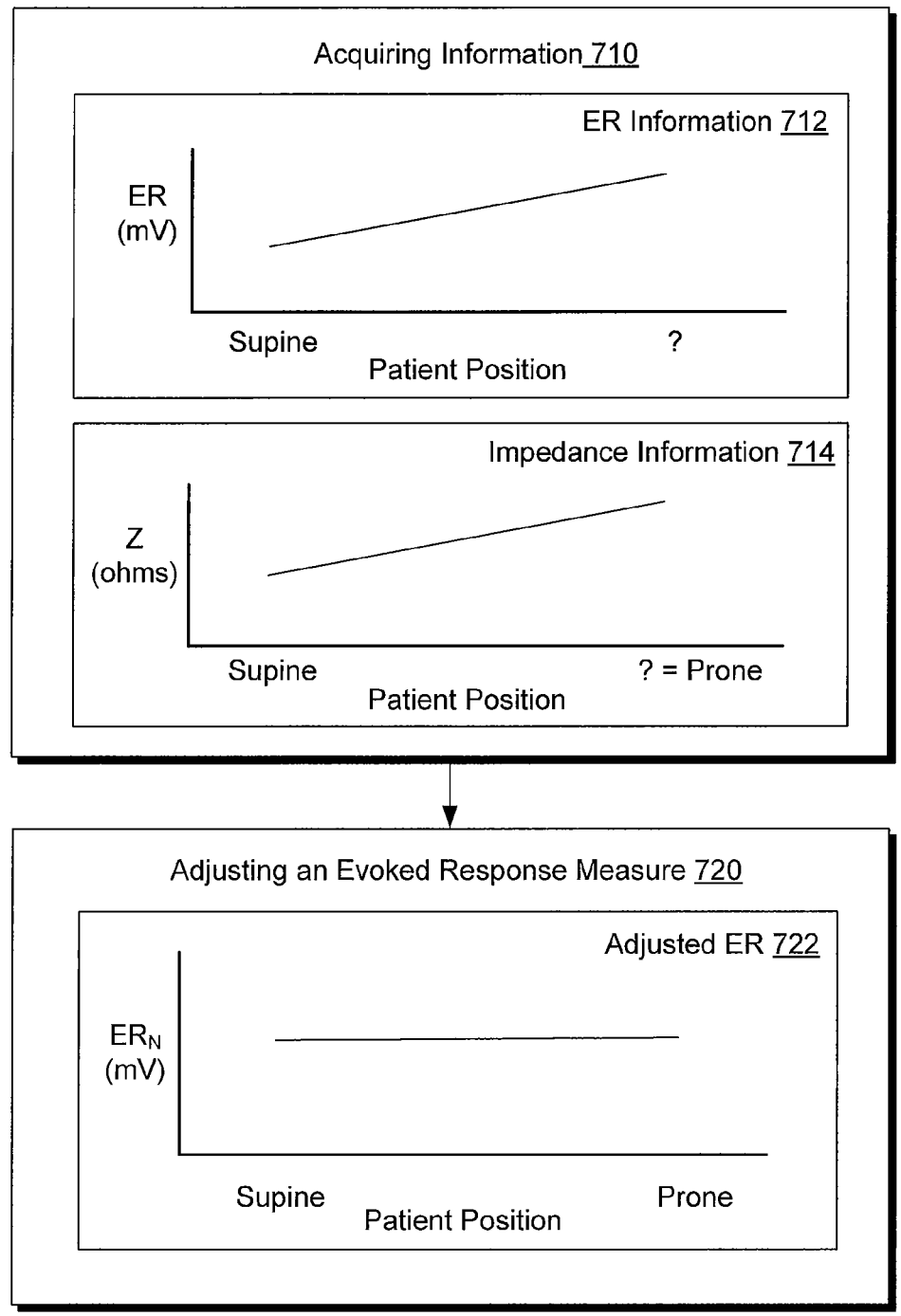
FIG. 7 is a series of plots related to an exemplary method of adjusting evoked response information based on impedance information.

FIG. 7 shows an exemplary method 700 that includes acquiring information 710 and then adjusting an evoked response measure based at least in part on the acquired information 720. In this example, evoked response information 712 is acquired while a patient is in a supine position and in a yet to be determined position ("?"). In a substantially contemporaneous manner, intrathoracic impedance information 714 is acquired that indicates the yet to be determined position is a prone position (i.e., "?=Prone"). An adjusted evoked response measure (i.e., normalized evoked response measure "$ER_N$") 722 is based at least in part on the acquired evoked response information 712 and the acquired impedance information 714. Such an exemplary method may be implemented using an implantable device where the device acquires the evoked response information and uses impedance information to make any adjustments to the acquired evoked response information.

Figure 8:
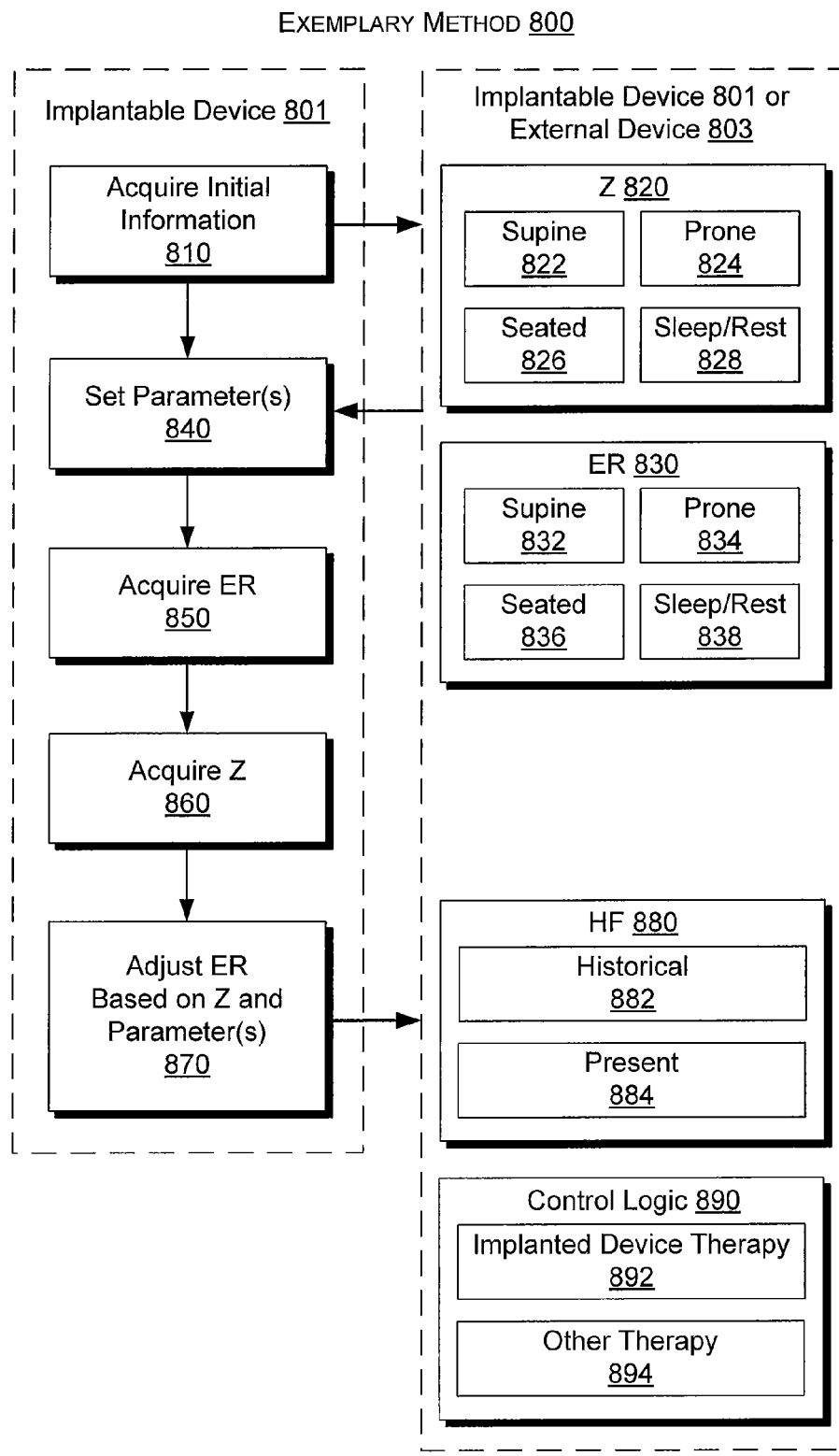
FIG. 8 is a block diagram of an exemplary method that also includes various components for implementation of such a method.

FIG. 8 shows an exemplary method 800 that is implemented using an implantable device 801 and optionally an external device 803 (e.g., a programmer for the implantable device 801, etc.). Accordingly, in FIG. 8, blocks 820, 830, 880 and 890 pertain to data and/or control logic, which may be part of the implantable device 801 and/or the external device 803, and the blocks 810, 840, 850, 860 and 870 pertain to actions typically taken by the implantable device 801.

The exemplary method 800 includes an acquisition block 810 for acquiring initial information (e.g., data) using the implantable device 801. Such initial information may include impedance information 820 and evoked response information 830. The exemplary techniques discussed with respect to the method 600 of FIG. 6 may be applied to the impedance information 820 and/or the evoked response information 830. For example, the impedance information 820 and/or the evoked response information 830 may include filtered information (see, e.g., the filters 610 of FIG. 6).

In the example of FIG. 8, the impedance information "Z" 820 includes information acquired while a patient is in various positions and/or activity states. For example, impedance information 820 may include supine impedance information 822, prone impedance information 824, seated impedance information 826 and/or sleep/rest impedance information 828. Such information may be acquired by the implantable device 801 and stored by the implantable device 801 or communicated to the external device 803. Similarly, evoked response information 830 may include supine evoked response information 832, prone evoked response information 834, seated evoked response information 836 and/or sleep/rest impedance information 838. Such information may be acquired by the implantable device 801 and stored by the implantable device 801 or communicated to the external device 803.

The exemplary method 800 may rely on a table of information such as Table 1 (below):

TABLE 1

Baseline Measurements of ER and Z at different postures

| Posture | ER | % change ER | Z of Can-RV$_{tip}$ | % change Z |
|---|---|---|---|---|
| Sitting | | | | |
| Standing | | | | |
| Supine | | | | |
| Nominal | | | | |

With respect to Table 1, the stimulus that causes the evoked response may be delivered using an electrode configuration that differs from the electrode configuration used to acquire the evoked response information. The electrode configuration used for acquisition of impedance information may be the same as that used for acquisition of the evoked response information or it may differ. In general, the electrode configuration used for acquisition of the impedance information has a substantial maximum interelectrode spacing (e.g., typically greater than a few centimeters).

The exemplary method 800 includes a parameter set block 840 that sets one or more parameters that pertain to a relationship between evoked response information and impedance information. For example, the implantable device 801 or the external device 803 may use the information 820, 830 to determine one or more parameters for a model that establishes a relationship between evoked response information and impedance information. In particular, a relationship may exist for adjusting evoked response measures based at least in part on impedance information, especially where evoked response information exists for more than one patient position.

In an evoked response acquisition block 850, the exemplary method 800 acquires evoked response information using the implantable device 801. Similarly, in an impedance acquisition block 860, the exemplary method 800 acquires impedance information using the implantable device 801. An adjustment block 870 then adjusts, as appropriate, the evoked response information acquired in the acquisition block 850 using the one or more parameters (block 840) and the impedance information acquired in the acquisition block 860.

As already mentioned, adjustments to evoked response information may aid in assessing cardiac condition. As shown in FIG. 8, heart failure information 880 is stored in the implantable device 801 or the external device 803. In this example, the heart failure information 880 includes historical information 882 and present information 884, which may be information recently downloaded from the implantable device 801 to the external device 803. Of course, after some time, such "present" information 884 can become historical information 882.

As described herein, the heart failure information 880 allows for diagnosis of patient condition and optionally selection of a patient therapy. For example, consider the information in the plot 400 of FIG. 4 where evoked response information correlates with progression of heart failure. The exemplary method 800 can increase accuracy of such information and thereby allow for a more accurate assessment of patient condition and optional selection of therapy.

The exemplary method 800 may include selecting an implantable device therapy or other therapy based at least in part on adjusted evoked response information (e.g., per block 870) and optionally other evoked response information (e.g., not adjusted by impedance information). Such selecting may rely on control logic 890 (of the implantable device 801 or the external device 803) to determine or select an implantable device therapy (e.g., logic 892) or other therapy (e.g., logic 894). In general, such logic is implemented using processor executable instructions which may be stored on one or more computer-readable media. Alternatively, or in addition to such control logic, a care provider may make such therapy selections or interact with the device 801 or 803 to make such therapy selections.

Thus, the exemplary method 800 may be implemented using an implantable device such as the device 100 of FIG. 1 or it may be implemented using an implantable device and an external device such as, but not limited to, an implantable device programmer.

Figure 9:
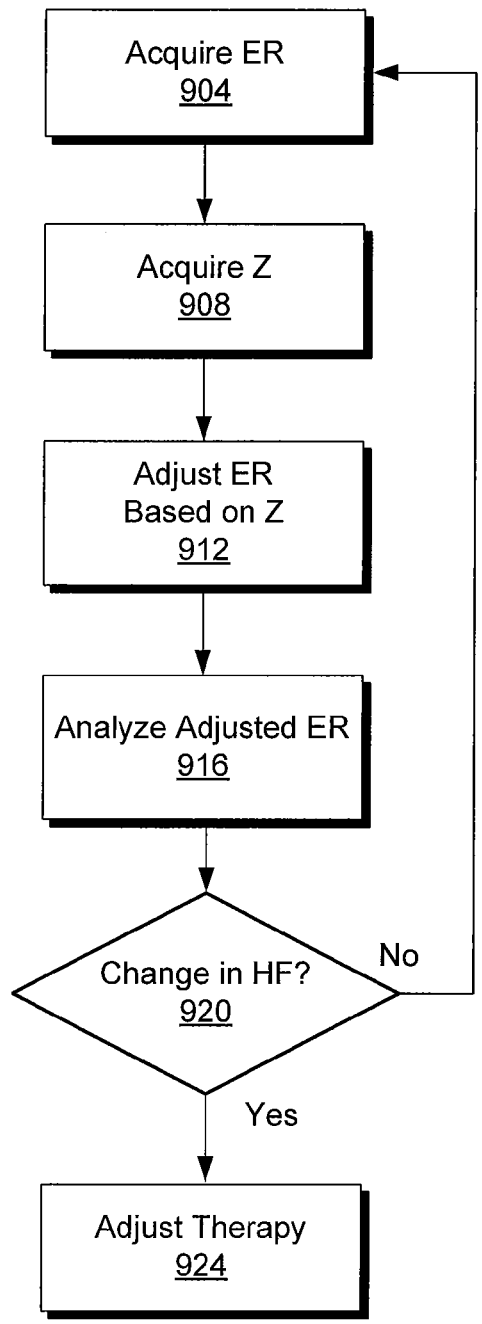
FIG. 9 is a block diagram of an exemplary method for optionally adjusting therapy based at least in part on evoked response information.

FIG. 9 shows an exemplary method 900 for adjusting patient therapy. The method 900 commences in an acquisition block 904 for acquiring evoked response information. An acquisition block 908 for acquiring impedance information operates substantially contemporaneously with the acquisition block 904. For example, where a patient changes position, the information acquired in blocks 904 and 908 typically acquire information at least before and after or during the change in position.

According to the exemplary method 900, an adjustment block 912 adjusts the evoked response information (per block 904), as appropriate, based at least in part on the acquired impedance information (per block 908). An analysis block 916 follows that analyzes the adjusted evoked response information, optionally in conjunction with other information such as, but not limited to, evoked response information that has not been adjusted using impedance information.

A decision block 920 then decides whether a change has occurred in cardiac condition (e.g., heart failure) based at least in part on the analysis. For example, the decision block 920 may rely on the analysis of block 916 as well as one or more criteria and/or historical information. If the decision block 920 decides that a change in cardiac condition has not occurred (e.g., less than some limit), then the method 900 continues in the acquisition block 904. However, if the decision block 920 decides that a change has occurred in cardiac condition, then the method 900 enters an adjustment block 924 that adjusts therapy. For example, a pacing rate, a VV delay (e.g., bi-ventricular pacing), an AV delay, etc., may be adjusted or selected based on the decision 920.

In general, the adjustment block 924 adjusts therapy in a manner whereby a stimulation or pacing therapy continues and thus allows for acquisition of further evoked response information. In such instances, the method 900 may continue at block 904. However, where an adjustment in therapy leads to no further pacing, then delivery of stimulation for acquisition of evoked response information may be contraindicated.

FIG. 10 shows two schemes 1000 for delivery of pacing stimuli: a constant voltage scheme 1010 and a constant current scheme 1020. As described herein a constant current scheme 1020 can reduce the effect of patient position on evoked response information. Such a scheme may be implemented for certain periods of time where evoked response information is acquired for use in assessing cardiac condition. At other times, a constant voltage scheme 1010 or other scheme may be used. Of course, evoked response information acquired using any of a variety of schemes may be analyzed to assess cardiac condition. Again, the exemplary scheme 1020 particularly aims to increase accuracy of such assessments.

With reference to the device 100 of FIGS. 1 and 2, the output of a stimulus may be measured in volts, units of electrical potential difference. The difference in electrical potential pushes current through the pacing lead and the heart (and optionally other media, e.g., blood). The current, measured in amps, is the electron flow rate. Resistance, measured in ohms, is the opposition to current. The amount of current can be estimated by dividing the difference in voltage by the resistance, which is referred to herein as impedance, more specifically the interelectrode impedance for the electrodes used to deliver a stimulus.

The constant voltage scheme 1010 involves producing the same voltage difference to the lead regardless of interelectrode resistance. As the interelectrode resistance increases, the current decreases, maintaining a constant voltage output.

The constant current scheme 1020 involves varying the output voltage in proportion to the interelectrode resistance. As the interelectrode resistance increases, the voltage increases to maintain a constant current level.

The constant voltage scheme 1010 relies on a constant potential difference between two electrodes: $\Delta V = |V_2 - V_1|$. Impedance exists between the two electrodes, which, in turn, determines the current flow in the conductive medium or media (e.g., myocardium, blood, etc.). Current decreases as impedance increases; thus, if impedance increases upon standing, then current will decrease and thereby to some extent effect evoked response.

In contrast, the constant current scheme 1020 relies on a delivery of a constant current. Thus, if impedance increases due to standing, the potential difference between the electrodes increases. A change in potential typically has less effect on evoked response information than a change in current. Hence, the constant current approach can reduce the effect of patient posture on evoked response information.

The constant current scheme 1020 is particularly useful where a bipolar electrode configuration is used for delivery of stimuli. Of course, changes in "constant" voltage or "constant" current will occur where the capture threshold changes. Capture threshold and impedance each provide information about a pacing system. Capture threshold may also be discussed in terms of charge and energy and in relation to the width of a stimulation pulse.

Figure 11:
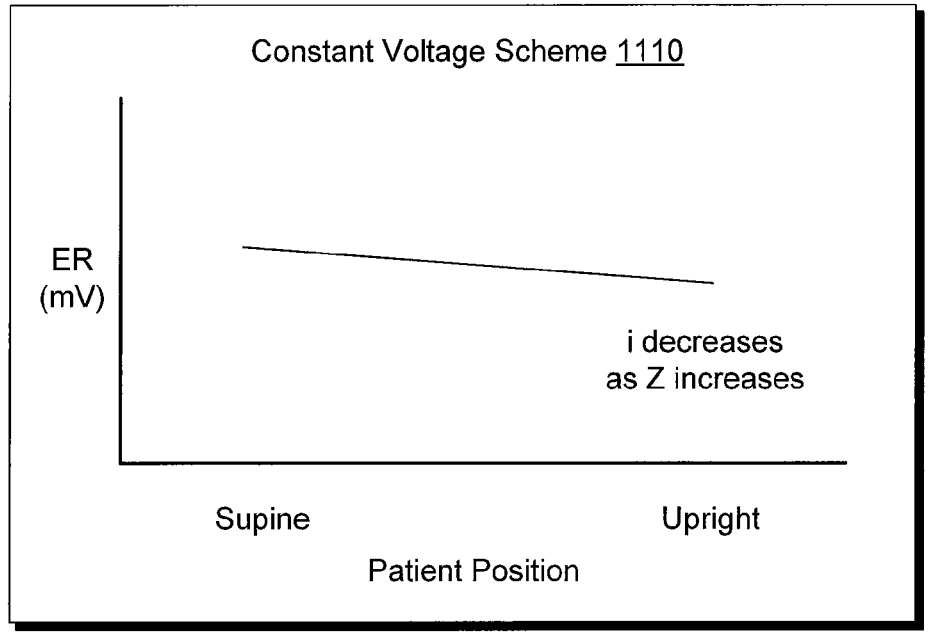
FIG. 11 is a series of plots where each plot corresponds to a particular pacing scheme.
Figure 11:
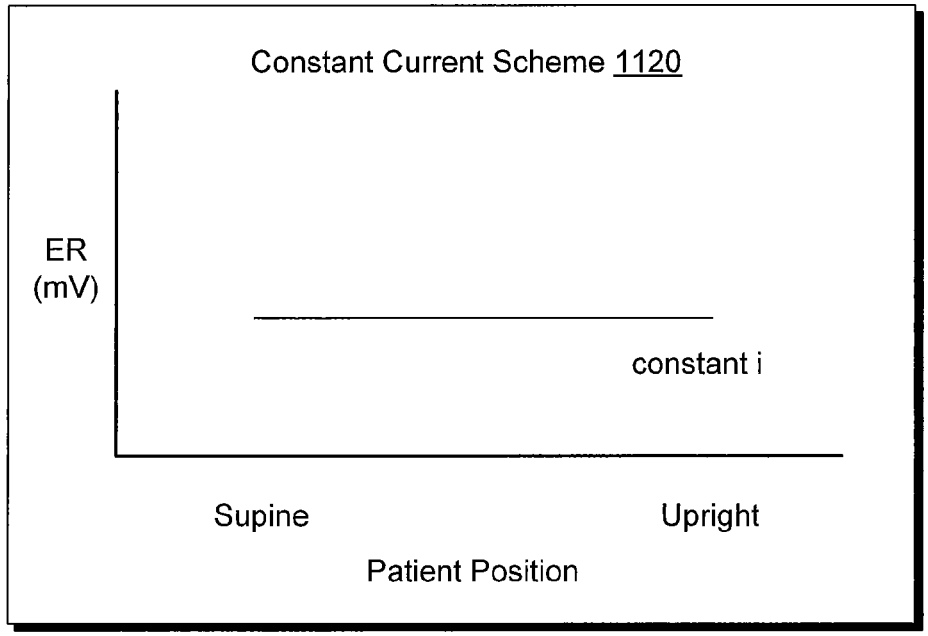

FIG. 11 shows two evoked response versus patient position plots for two bipolar pacing schemes 1100: constant voltage and constant current. The plots 1110 and 1120 focus specifically on interelectrode effects related to the stimulation electrodes and do not portray other effects, for example, the effect a change in patient position has on an evoked response measured using an electrode configuration that differs from the electrode configuration used to deliver the stimulation.

The plot 1110 pertains to a constant voltage scheme whereby a change in patient position from supine to upright causes an increase in interelectrode impedance and a decrease in current. As a consequence, the evoked response amplitude decreases. In contrast, the plot 1120 pertains to a constant current scheme whereby a change in patient position from supine to upright causes no change in current. Thus, the evoked response amplitude does not exhibit a change like that of the plot 1110.

An exemplary method may use the scheme 1110, the scheme 1120 or both over a period of time. In the constant current scheme 1120, impedance may be acquired and used to adjust voltage, if necessary, maintain effective constant current pacing. The constant current scheme 1120 is particularly suited to multi-polar electrode configurations where distance between the electrodes is considerably less than that of a typical unipolar can to tip electrode configuration. For example, with smaller inter-electrode spacing, a bipolar electrode configuration using a ring and tip electrode on the same lead, use of constant current helps to minimize the effect of impedance changes between the electrodes. However, in some instances, a goal may be to maximize the effect of impedance or to acquire a signal influenced by impedance changes. In such instances, a constant voltage scheme may be used or the constant voltage 1010 and constant current schemes 1020 may be both used and acquired information compared. In general, bipolar pacing and sensing (e.g., ring-tip configuration) act to minimize effects impedance due to respiration, patient position changes, and the like.

An exemplary method monitors an evoked response measure for progression of heart failure. For example, such a method may acquire unipolar (can to $RV_{tip}$ electrodes) cardiac electrograms and scale information in the cardiac electrograms inversely by a change in impedance between the electrodes (e.g., can and $RV_{tip}$ electrodes), where the impedance measured at or at about the same time as the evoked response (e.g., same heart beat, within +/-10 heart beats or other period). The measured impedance may be used to calculate a percentage change from a nominal impedance value (e.g., a long-term average). In turn, the percentage change in impedance may be used to scale inversely an ER measure. For example, if impedance (Z) decreased by 20%, then the ER measure could be scaled by 120% to compensate for an expected decrease in ER due to the change in impedance (Z). A nominal value for impedance may be determined according to a baseline, running average, etc. The nominal value may be set based at least in part on patient risk of heart failure or other condition. For example, where risk is high, then the nominal value may be based on a running average over a day to about a week. Where risk is less, then the running average may extend to several weeks or a month. Such determinations may be made on the basis of NYHA class (e.g., class II=x weeks, class III=1 week, class IV=1 day). While various examples mention unipolar can-$RV_{tip}$ configurations, other multipolar (e.g., bipolar, etc.) and unipolar sensing configurations are also applicable such as, but not limited to, can-$LV_{tip}$, those with $RV_{ring}$, $LV_{ring}$, SVC electrodes, etc.

An exemplary method may establish a baseline where both ER and Z information are acquired. Such a method may then establish a relationship between a change in Z and a change in ER. In this example, if Z decreased by 20%, and the corresponding pre-determined ER change at the baseline was 15%, then the ER measure may be scaled by 115% (i.e., 100%+ 15%) to compensate the decrease in ER due to the change in Z.

Various exemplary methods, devices, systems, etc., use an evoked response PDI to determine patient condition or appropriate therapy. Various exemplary methods, devices, systems, etc., use impedance such as an intrathoracic impedance to determine patient condition or appropriate therapy. Of course, a combination of IEGM information and impedance information may be used for monitoring or selection of therapy. Changes in values over time, based on such information, may be used to determine condition or appropriate therapy. For example, consider a parameter "ΔS", where "S" may be any of a variety of parameters (e.g., ER Span, $Z_R$ Span, number of breaths per unit time, etc.). A daily ΔS value may be determined or another time basis may be used. Of course, use of other bases are possible such as, but not limited to, posture, medication-related, pacing therapy-related, etc.

While various exemplary methods, devices, systems, etc., include capabilities to monitor patient position (e.g., via an accelerometer), posture testing may be performed and then relevant information communicated to an exemplary implantable device via a programmer.

CONCLUSION

Although exemplary mechanisms (e.g., implemented as or in methods, devices, systems, software, etc.) have been described in language specific to structural features and/or methodological acts, it is to be understood that the subject matter defined in the appended claims is not necessarily limited to the specific features or acts described.

What is claimed is:

1. A method comprising:
    acquiring intrathoracic impedance values over one or more respiratory cycles for a patient in a prone position;
    acquiring intrathoracic impedance values over one or more respiratory cycles for a patient in a supine position;
    determining a difference between the intrathroacic impedance values for the patient in the prone position and for the patient in the supine position; and
    conditionally adjusting as appropriate one or more evoked response values using the difference.

2. The method of claim 1 wherein the adjusting adjusts the one or more evoked response values inversely to the difference.

3. The method of claim 1 further comprising assessing cardiac condition of the patient based at least in part on the adjusting.

4. The method of claim 1 further comprising acquiring the one or more evoked response values using an intracardiac electrode.

5. The method of claim 4 wherein the one or more evoked response values correspond to one or more evoked responses to constant current cardiac pacing stimuli.

6. The method of claim 1 wherein the intrathoracic impedance values correspond to a unipolar electrode configuration and wherein the one or more evoked responses values correspond to a unipolar electrode configuration.

7. The method of claim 6 wherein the unipolar electrode configurations are the same unipolar electrode configuration.

8. The method of claim 1 wherein the acquiring acquires the intrathoracic impedance values substantially contemporaneous to acquisition of cardiac electrograms for the one or more evoked response values.

9. An implantable device comprising:
    a processor;
    memory; and
    control logic configured to call for acquiring intrathoracic impedance values over one or more respiratory cycles for a patient in a prone position, to call for acquiring intrathoracic impedance values over one or more respiratory cycles for a patient in a supine position, to determine a difference between the intrathroacic impedance values for the patient in the prone position and for the patient in the supine position, and to conditionally adjust as appropriate one or more evoked response values using the difference.

10. The implantable device of claim 9 wherein the control logic comprises processor executable instructions stored in the memory.

11. The implantable device of claim 9 wherein the intrathoracic impedance values and the one or more evoked responses values correspond to a unipolar electrode configuration.

12. An implantable cardiac system comprising:
    means for acquiring intrathoracic impedance values over one or more respiratory cycles for a patient in a prone position;
    means for acquiring intrathoracic impedance values over one or more respiratory cycles for a patient in a supine position;
    means for determining a difference between the intrathroacic impedance values for the patient in the prone position and for the patient in the supine position; and
    means for conditionally adjusting as appropriate one or more evoked response values using the difference.

13. The implantable cardiac system of claim 12 wherein the means for adjusting comprises means for adjusting the one or more evoked response values inversely to the difference.

14. The implantable cardiac system of claim 12 further comprising means for assessing cardiac condition of the patient based at least in part on the means for adjusting.

15. The implantable cardiac system of claim 12 further comprising means for acquiring the one or more evoked response values using an intracardiac electrode.

16. The implantable cardiac system of claim 15 wherein the one or more evoked response values correspond to one or more evoked responses to constant current cardiac pacing stimuli.

17. The implantable cardiac system of claim 12 wherein the intrathoracic impedance values and the one or more evoked responses values correspond to a unipolar electrode configuration.

* * * * *